United States Patent [19]

Bodor et al.

[11] 4,279,900

[45] Jul. 21, 1981

[54] PRODRUGS FOR THE IMPROVED DELIVERY OF HALOGEN-CONTAINING GLUCOCORTICOSTEROIDS

[75] Inventors: Nicholas S. Bodor, Gainesville, Fla.; Kenneth B. Sloan, Eudora, Kans.

[73] Assignee: Intrex Research Corporation, Lawrence, Kans.

[21] Appl. No.: 61,177

[22] Filed: Jul. 27, 1979

Related U.S. Application Data

[63] Continuation-in-part of Ser. No. 924,304, Jul. 13, 1978, abandoned.

[51] Int. Cl.$^3$ .............................................. A61K 3/58
[52] U.S. Cl. .............................. 424/241; 260/239.5; 260/239.55 D
[58] Field of Search ...................... 260/239.5; 424/241

[56] References Cited

U.S. PATENT DOCUMENTS

| 3,357,972 | 12/1967 | Deason | 260/239.5 |
| 4,069,322 | 1/1978 | Bodor et al. | 260/239.5 |

*Primary Examiner*—Elbert L. Roberts
*Attorney, Agent, or Firm*—Burns, Doane, Swecker & Mathis

[57] ABSTRACT

Novel 3,2'-spiro(1',3'-thiazolidine) compounds which are transient prodrug forms of known 6- and/or 9-haloglucocorticosteroids are described. The subject prodrugs provide improved delivery of the prior art steroids for therapeutic purposes, particularly in alleviating inflammation, and can be prepared by known methods, for example, by reacting the corresponding 3-keto steroids with a thiazolidine forming reagent such as an L-cysteine alkyl ester.

67 Claims, No Drawings

PRODRUGS FOR THE IMPROVED DELIVERY OF HALOGEN-CONTAINING GLUCOCORTICOSTEROIDS

CROSS-REFERENCE TO RELATED APPLICATION

This application is a continuation-in-part of our earlier copending application, Ser. No. 924,304, filed July 13, 1978, now abandoned assigned to the assignee hereof and hereby expressly incorporated by reference in its entirety and relied upon.

TECHNICAL FIELD OF THE INVENTION

The present invention relates to certain selected novel 3,2'-spiro(1',3'-thiazolidine) steroids which are transient prodrug forms of conventional 6- and/or 9-haloglucocorticosteroids (e.g., fludrocortisone acetate, triamcinolone acetonide, betamethasone, dexamethasone, and the like) useful as pharmaceuticals, particularly in alleviating inflammatory conditions in warm-blooded animals.

For purposes of this specification, the term "prodrug" denotes a derivative of a known and proven prior art 6- and/or 9-halocorticosteroid compound (e.g., fludrocortisone acetate, triamcinolone acetonide, betamethasone, dexamethasone, or the like), which derivative, when administered to a warm-blooded animal, "cleaves" in such a manner as to release the proven drug form at its target site or sites of activity.

The term "transient" denotes enzymatic and/or chemical hydrolytic "cleavage" of the compounds of the present invention in a manner such that the proven drug form (the conventional antiinflammatory steroid, e.g., fludrocortisone acetate, triamcinolone acetonide, betamethasone, dexamathasone, or the like) is released, while the remaining "cleaved" moiety remains nontoxic and is metabolized in such a manner that nontoxic, metabolic products are produced.

Finally, the term "pharmaceutically acceptable acid addition salt" as used herein generally includes the nontoxic acid addition salts of selected compounds of formula (I), formed with nontoxic inorganic or organic acids. For example, the salts include those derived from inorganic acids such as hydrochloric, hydrobromic, sulfuric, sulfamic, phosphoric, nitric and the like; and the salts prepared from organic acids such as acetic, propionic, succinic, glycollic, stearic, lactic, malic, tartaric, citric, ascorbic, pamoic, maleic, hydroxymaleic, phenylacetic, glutamic, benzoic, salicyclic, sulfanilic, fumaric, sulfonic, toluenesulfonic, and the like.

BACKGROUND OF THE PRIOR ART

Conventional anti-inflammatory halogen-containing steroids, such as fludrocortisone acetate, triamcinolone acetonide, betamethasone, dexamethasone, and the like, are high molecular weight steroidal compounds containing a number of hydrophilic functions. e.g., hydroxyl and keto functions. These compounds are characterized as having (1) extremely low water solubility, (2) extensive intermolecular hydrogen bonding due to the combination of hydrophilic functions, such as —OH and =O (as evidenced by their high melting point), and (3) high molecular weight.

All three points enumerated above contribute to the inefficient and slow penetrability of these conventional steroidal compounds through biological barriers, among which the most important are (i) the skin and (ii) the gastrointestinal wall.

It is recognized that in the case of the skin, the high molecular weight anti-inflammatory steroids are absorbed primarily through the appendages and the hair follicles as opposed to the more efficient molecular intecellular absorption. See M. Katz and B. J. Poulsen, "Absorption of Drugs Through the Skin", Handbook of Experimental Pharmacology, Vol. XXVII/I, Chapter 7, page 104, Springer Verlag, Berlin—Heidelberg—New York (1971).

It too is art recognized that: (4) a serious side effect of certain of the known anti-inflammatory steroids is the decrease in thickness, or atrophy, of the skin at the site of application; that (5) another adverse effect is a deleterious, systemic side effect on the thymus gland; and that (6) in certain instances, with certain of the derivatives, the reduction of inflammation is inadequate.

In view of the foregoing, it is apparent that a serious need exists for a class of novel anti-inflammatory steroidal compounds which will overcome the aforementioned inefficiencies such that penetration of the same through biological barriers will be enhanced, such that less atrophy results, such that less effect on the thymus gland is evidenced, and such that inflammation is significantly reduced.

SUMMARY OF THE INVENTION

It is one object of the present invention to provide prodrug forms of conventional anti-flammatory halosteroids which possess the capability of efficiently penetrating the biological barriers of warm-blooded animals, and, especially, the skin and the gastrointestinal wall.

Another object is the provision of prodrugs of conventional anti-inflammatory halogen-containing steroids which cause less atrophy, systemically affect the thymus to a much lesser degree, but which, nonetheless, remain highly potent.

It is another object of the present invention to provide such prodrug forms of conventional anti-inflammatory compounds which, following administration, will "cleave" in such a manner as to enable the original parent steroidal moiety (e.g., fludrocortisone acetate, triamcinolone acetonide, betamethasone, dexamethasone, or similar compound) to be released at its therapeutic site or sites of anti-inflammatory activity and to further permit the cleaved moiety(ies) unassociated with the parent steroidal moiety to be metabolized in a nontoxic fashion.

All the foregoing objects are achieved by topically or orally administering to a warm-blooded animal afflicted with inflammation, a therapeutically effective anti-inflammatory amount of a compound having the structural formula:

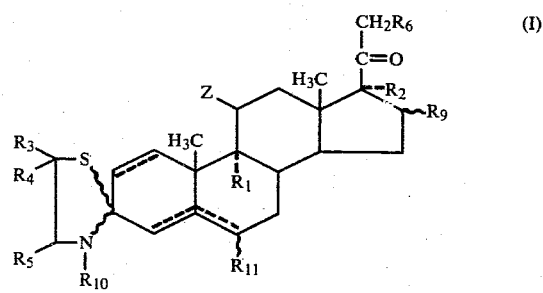

wherein $R_1$ and $R_{11}$ are each H, F or Cl, with the proviso that $R_1$ and $R_{11}$ cannot simultaneously be H; $R_2$ is OH, —OCOR$_7$, —OCOR$_8$, or $C_1$-$C_{10}$ alkyl; $R_3$ and $R_4$ may be the same or different and are each H or $C_1$-$C_8$ alkyl; $R_5$ is H or —COOR$_7$; $R_6$ is OH, F, Cl, Br or —OCOR$_8$; $R_7$ is H, $C_1$-$C_{20}$ alkyl, $C_2$-$C_{20}$ alkenyl, $C_5$-$C_7$ cycloalkyl, $C_5$-$C_7$ cycloalkyl-$C_6$-$C_{10}$ aryl, phenyl or $C_1$-$C_4$ alkyl-substituted phenyl; $R_8$ is $C_1$-$C_{20}$ alkyl, $C_2$-$C_{20}$ alkenyl, $C_5$-$C_7$ cycloalkyl, $C_5$-$C_7$ cycloalkyl-$C_6$-$C_{10}$ aryl, phenyl, $C_1$-$C_4$ alkyl-substituted phenyl, —(CH$_2$)$_n$COOH wherein n is an integer of 1 to 5, or —(CH$_2$)$_n$CON(R$_7$)$_2$ wherein n and $R_7$ are defined as above, or $R_8$ is

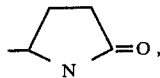

or a 2,3 or 4 pyridyl, wherein at least one of the hydrogen atoms therein can be replaced by a member selected from the group consisting of —N(R$_4$)$_2$, —CON(R$_4$)$_2$, —SOR$_4$, a halogen atom (Cl, Br, I) —COOR$_4$, —COOCH$_2$N(R$_4$)$_2$ and —COOCH$_2$—S—R$_4$, wherein $R_4$ is defined above; $R_9$ is H, $C_1$-$C_8$ alkyl, F, Cl or OH; or $R_2$ and $R_9$ may be combined to form a cyclic ketal of the formula

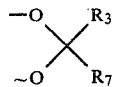

wherein $R_3$ and $R_7$ are defined as above; $R_{10}$ is H, —COR$_7$ or —COOR$_7$ wherein $R_7$ is defined as above, with the proviso that when $R_{10}$ is H, then the compound of formula (I) can be in the form of a pharmaceutically acceptable acid addition salt; Z is =O, β—OH or β—OCOR$_7$ wherein $R_7$ is defined as above; the dotted line at the 1(2)-position indicates the presence of an optional double bond; the dotted lines at the 4(5) - and 5(6)-positions indicate the presence of a double bond at either the 4(5) - or the 5(6) position; and the wavy lines indicate the α or β-configuration.

DETAILED DESCRIPTION OF THE INVENTION

All of the compounds encompassed by formula (I) above essentially satisfy the objectives of the present invention. However, a preferred group of compounds consists of those comounds of formula (I) wherein $R_3$, $R_4$, $R_5$ and $R_{10}$ are as hereinbefore defined and the remainder of the structural variables are identical to those found in any one of the following known anti-inflammatory halogen-containing steroids: fludrocortisone, fludrocortisone acetate, flurandrenolone acetonide (flurandrenolide), amcinafal, amcinafide, betamethasone, betamethasone benzoate, betamethasone valerate, betamethasone dipropionate, chloroprednisone acetate, dexamethasone, difluprednate, flumethasone, flumethasone pivalate, flunisolide acetate, fluocinolone acetonide, fluocinonide, fluprednisolone, fluprednisolone valerate, paramethasone, paramethasone acetate, triamcinolone, triamcinolone acetonide, triamcinolone hexacetonide and triamcinolone diacetate. An especially preferred group of compounds consists of the compounds of formula (I) wherein $R_3$ and $R_4$ are each hydrogen or methyl, $R_5$ is —COOR$_7$' wherein $R_7$' is H, $C_1$-$C_{20}$ alkyl or benzyl, $R_{10}$ is H and the remainder of the structural variables are identical to those of any one of the aforementioned known 6- and/or 9-halocorticosteroid anti-inflammatory agents, most especially preferred compounds being those wherein $R_5$ is —COOR$_7$' wherein $R_7$' is alkyl of 1 to 12 carbon atoms.

Preferred specific embodiments of the present invention are the selected compounds set forth immediately below:

(1) 21-Acetyloxy-9α-fluoro-11β,17α-dihydroxypregn-4-en-20-one-3,2'-spiro(4'-carboethoxy-1',3'-thiazolidine);

(2) 21-Acetyloxy-9α-fluoro-11β,17α-dihydroxy-16α-methylpregn-4-en-20-one-3,2'-spiro(4'-carboethoxy-1',3'-thiazolidine);

(3) 21-Acetyloxy-9α-fluoro-11β,16α,17α-trihydroxypregn-4-en-20-one-3,2'-spiro(4'-carboethoxy-1',3'-thiazolidine);

(4) 9α-Fluoro-11β,21-dihydroxy-16α,17α-[(1-methylethylidene)bis (oxy)]pregna-1,4-dien-20-one-3,2'-spiro(4'-carboethoxy-1',3'-thiazolidine);

(5) 9α-Fluoro-11β,21-dihydroxy-16α,17α-[(1-methylethylidene)bis(oxy)]pregna-1,4-dien-20-one-3,2'-spiro-(4'-carbohexoxy-1',3'-thiazolidine);

(6) 9α-Fluoro-11β,21-dihydroxy-16α,17α-[(1-methylethylidene)bis(oxy)]pregna-1,4-dien-20-one-3,2'-spiro(4'-carbodecoxy-1',3'-thiazolidine);

(7) 21-Acetyloxy-9α-fluoro-11β-hydroxy-16α,17α-[(1-methylethylidene)bis(oxy)]pregna-1,4-dien-20-one-3,2'-spiro(4'-carboethoxy-1',3'-thiazolidine);

(8) 21-Acetyloxy-9α-fluoro-11β-hydroxy-16α,17α-[(1-methylethylidene)bis(oxy)]pregna-1,4-dien-20-one-3,2'-spiro(4'-carbohexoxy-1',3'-thiazolidine);

(9) 21-Acetyloxy-9α-fluoro-11β-hydroxy-16α,17α-[(1-methylethylidene)bis(oxy)]pregna-1,4-dien-20-one-3,2'-spiro(4'-carbodecoxy-1',3'-thiazolidine);

(10) 9α-Fluoro-11β,17α,21-trihydroxy-16β-methylpregna-1,4-dien-20-one-3,2'-spiro(4'-carboethoxy-1',3'-thiazolidine);

(11) 9α-Fluoro-11β,17α,21-trihydroxy-16β-methylpregna-1,4-dien-20-one-3,2'-spiro(4'-carbohexoxy-1',3'-thiazolidine);

(12) 9α-Fluoro-11β,17α,21-trihydroxy-16β-methylpregna-1,4-dien-20-one-3,2'-spiro(4'-carbodecoxy-1',3'-thiazolidine);

(13) 9α-Fluoro-11β,17α,21-trihydroxy-16α-methylpregna-1,4-dien-20-one-3,2'-spiro(4'-carboethoxy-1',3'-thiazolidine);

(14) 9α-Fluoro-11β,17α,21-trihydroxy-16α-methylpregna-1,4-dien-20-one-3,2'-spiro(4'-carbohexoxy-1',3'-thiazolidine);

(15) 9α-Fluoro-11β,17α,21-trihydroxy-16α-methylpregna-1,4-dien-20-one-3,2'-spiro(4'-carbodecoxy-1',3'-thiazolidine);

(16) 9α-Fluoro-11β,17α-dihydroxy-16β-methyl-21-valeryloxypregna-1,4-dien-20-one-3,2'-spiro(4'-carboethoxy-1',3'-thiazolidine);

(17) 9α-Fluoro-11β,17α-dihydroxy-16β-methyl-21-valeryloxypregna-1,4-dien-20-one-3,2'-spiro-(4'-carbohexoxy-1',3'-thiazolidine);

(18) 9α-Fluoro-11β,17α-dihydroxy-16β-methyl-21-valeryloxypregna-1,4-dien-20-one-3,2'-spiro(4'-carbodecoxy-1',3'-thiazolidine);

(19) 9α-Fluoro-11β,21-dihydroxy-16β-methyl-17α-valeryloxypregna-1,4-dien-20-one-3,2′-spiro(4′-carboethoxy-1′,3′-thiazolidine);

(20) 9α-Fluoro-11β,21-dihydroxy-16β-methyl-17α-valeryloxypregna-1,4-dien-20-one-3,2′-spiro(4′-carbohexoxy-1′,3′-thiazolidine);

(21) 9α-Fluoro-11β,21-dihydroxy-16β-methyl-17α-valeryloxypregna-1,4-dien-20-one-3,2′-spiro(4′-carbodecoxy-1′,3′-thiazolidine);

(22) 9α-Fluoro-11β,17α,21-trihydroxy-16α-methylpregna-1,4-dien-20-one-3,2′-spiro(4′-carboethoxy-5′,5′-dimethyl-1′,3′-thiazolidine);

(23) 9α-Fluoro-11β,17α,21-trihydroxy-16α-methylpregna-1,4-dien-20-one-3,2′-spiro(4′-carboethoxy-5′,5′-dimethyl-1′,3′-thiazolidine);

(24) 9α-Fluoro-11β,17α,21-trihydroxy-16α-methylpregna-1,4-dien-20-one-3,2′-spiro(4′-carbodecoxy-5′,5′-dimethyl-1′,3′-thiazolidine);

(25) 21-Chloro-9α-fluoro-11β,17α-dihydroxypregn-4-en-20-one-3,2′-spiro(4′-carboethoxy-1′,3′-thiazolidine);

(26) 21-Chloro-9α-fluoro-11β,17α-dihydroxypregn-4-en-20-one-3,2′-spiro(4′-carbomethoxy-1′,3′-thiazolidine);

(27) 21-Chloro-9α-fluoro-11β,17α-dihydroxypregn-4-en-20-one-3,2′-spiro(4′-carbodecoxy-1′,3′-thiazolidine);

(28) 21-Acetyloxy-9α-fluoro-11β,17α-dihydroxypregn-5-en-20-one-3,2′-spiro(4′-carboethoxy-1′,3′-thiazolidine);

(29) 21-Acetyloxy-9α-fluoro-11β,17α-dihydroxy-16α-methylpregn-5-en-20-one-3,2′-spiro(4′-carboethoxy-1′,3′-thiazolidine);

(30) 21-Acetyloxy-9α-fluoro-11β,16α,17α-trihydroxypregn-5-en-20-one-3,2′-spiro(4′-carboethoxy-1′,3′-thiazolidine);

(31) 21-Chloro-9α-fluoro-11β,17α-dihydroxypregn-5-en-20-one-3,2′-spiro(4′-carboethoxy-1′,3′-thiazolidine);

(32) 21-Chloro-9α-fluoro-11β,17α-dihydroxypregn-5-en-20-one-3,2′-spiro(4′-carbomethoxy-1′,3′-thiazolidine);

(33) 21-Chloro-9α-fluoro-11β,17α-dihydroxypregn-5-en-20-one-3,2′-spiro(4′-carbodecoxy-1′,3′-thiazolidine);

(34) 21-Acetyloxy-9α-fluoro-11β,17α-dihydroxypregn-4-en-20-one-3,2′-spiro(1′,3′-thiazolidine);

(35) 21-Acetyloxy-9α-fluoro-11β,17α-dihydroxypregn-5-en-20-one-3,2′-spiro(1′,3′-thiazolidine); and

(36) 9α-Fluoro-11β,21-dihydroxy-16α,17α-[(1-methylethylidene)bis(oxy)]pregna-1,4-dien-20-one-3,2′-spiro(1′,3′-thiazolidine).

The compounds of the present invention are easily prepared, utilizing known techniques. (Compare generally out U.S. Pat. No. 4,069,322, assigned to the assignee hereof and expressly incorporated by reference herein). Most conveniently, preparation involves contacting a compound corresponding to formula (I) but containing a 3-keto function, with a reagent of the formula

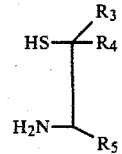

wherein $R_3$, $R_4$ and $R_5$ are hereinbefore defined, in the presence of a suitable organic solvent (e.g., benzene, toluene, xylene, dimethylformamide, or the like) and further in the presence of a suitable organic base (e.g. trimethylamine, triethylamine, pyridine, or the like). This reaction is carried out at standard pressure, at a temperature of from room temperature to the boiling point of the solvent employed and for a period of time ranging from approximately 2 to 48 hours. Alternatively, in this reaction, the organic base can serve as the solvent. In the course of the reaction, when the steroidal starting material is a $\Delta^4$ compound, the 4(5)-double bond sometimes migrates to the 5(6)-position.

Generally, a mixture of $\Delta^4$ and $\Delta^{5(6)}$ compounds results. The nature of the particular reagent of formula (II), e.g. whether the reagent is used in the form of the free base or in the form of its hydrochloride salt, and the nature of the steroidal starting material can influence the location of the double bond, as can the manner of isolation of the final product. While control of reaction conditions and isolation techniques so as to afford the $\Delta^4$ compounds is preferred because the $\Delta^4$ compounds on hydrolysis go directly to the parent hormone, the $\Delta^{5(6)}$ derivatives are also highly desirable because they readily undergo hydrolysis and rearrangement of the double bond to the $\Delta^4$ parent hormone.

The compounds resulting from the process described above are the compounds of formula (I) wherein $R_{10}$ is hydrogen. Further treatment of those products with a conventional acylating agent (e.g., acetic anhydride or propionic anhydride in pyridine) affords the corresponding compounds of the invention wherein $R_{10}$ is —$COR_7$ or —$COOR_7$.

A desirable alternate route to the compounds of formula (I) wherein the 1,2-linkage is unsaturated begins by reacting acetone with a reagent of formula (II) above. The product, a compound of the formula

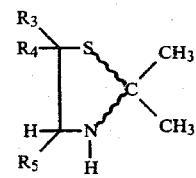

is then heated with a 3,20-diketosteroid, in the presence of an acid catalyst, using a large excess of the thiazolidine reactant, to effect transfer of the thiazolidine grouping to the steroid and provide the desired compound of formula (I).

The starting materials used in the preparation of the compounds of formula (I) can be prepared by known methods; thus, for example, the methods set forth in Example 1 below are applicable to the preparation of various compounds of formula (II).

The invention will appear more fully from the examples which follow. These examples are given by way of illustration only and are not to be construed as limiting the invention either in spirit or in scope as many modifications both in materials and methods will be apparent to those skilled in the art.

EXAMPLE 1

Illustrative Preparation of Starting Materials (a) L-Cysteine butyl ester hydrochloride:

L-Cysteine hydrochloride (100 g) is dissolved in 250 ml of butanol saturated with dry HCl. The solution is heated under reflux for 4 hours. Excess solvent is evaporated and ethyl acetate (150 ml) is added to the residue. The crystals which form are recrystallized from ethyl acetate, mp 91° C., yield 30%, IR (KBr)1745 cm$^{-1}$; NMR (CDCl$_3$) δ9.2–3.4 (b, 3, NH$_3^\oplus$), 4.7 (t, 1, —CH), 4.3 (t, 2, —OCH$_2$—), 3.3 (b, 2, CH$_2$S), 1.0 (5, 3, —CH$_3$), 1.0–3.0 (m, 4, —CH$_2$CH$_2$).

Anal. Calcd for C$_7$H$_{16}$ClNO$_2$S: C, 39.33; H, 7.54; N, 6.55. Found: C, 39.70; H, 7.59; N, 6.50.

(b) L-Cysteine hexyl ester hydrochloride:

L-Cysteine hydrochloride (78.5 g) is added to 150 ml of hexanol saturated with dry HCl gas. The mixture is heated under reflux overnight. The solution is evaporated to about half of the total volume, and then ethyl ether (150 ml) is added. The solution gives crystals when it is cooled. The crystals are filtered and are then recrystallized from ethyl acetate; yield 45 g; mp 89°–90° C.; IR (KBr) 1745 cm$^{-1}$; NMR (CDCl$_3$) δ9.2–8.4 (b, 3, NH$_3^\oplus$), 4.7 (t, 1, —CH—), 4.3 (t, 2, —OCH$_2$—), 3.4 (b, 2, CH$_2$S—), 1.0–3.0 (m, 8), 1.0 (t, 3—, CH$_3$).

Anal. Calcd for C$_9$H$_{20}$ClNO$_2$S: C, 44.69; H, 8.34; N, 5.79. Found: C, 44.80; H, 8.41; N, 5.69.

(c) L-Cysteine decyl ester hydrochloride:

L-Cysteine (157.4 g) is added to 250 ml of decyl alcohol saturated with dry HCl. The mixture is heated to 150° C. for 6 hours. The solution is cooled and then is mixed with an equal volume of ethyl acetate. The solution is cooled in a dry ice bath to give crystals. The crystals are filtered and are recrystallized from ethyl acetate, mp 96°–99° C., yield 100 g, IR (KBr) 1745 cm$^{-1}$; NMR (CDCl$_3$) δ8.4–9.2 (b, 3, NH$_3^{30}$), 4.7 (t, 1, —CH—), 4.3 (t, 2, —OCH$_2$—), 3.4 (b, 2, —CH$_2$S—), 1.0—3.0 (m, 16 —(CH$_2$)$_8$—), 2.6–2.8 (b, 1, SH), 1.0 (t, 3, CH$_3$—).

Anal. Calcd for C$_{13}$H$_{28}$NClSO$_2$: C, 52.51; H, 9.49; N, 4.71. Found: C, 52.20; H, 9.20; N, 4.80.

(d) Penicillamine ethyl ester hydrochloride:

Dry hydrogen chloride is bubbled through a suspension of penicillamine (25 g, 0.167 mole) in 300 ml of dry ethanol until all is in solution. The warm solution is then cooled in an ice bath to 0°–5° C. and saturated with dry HCl. The ice bath is removed and the reaction mixture is heated to reflux for 2 hours, then is concentrated in vacuo to a viscous golden oil which is cooled (−30° C.) overnight. After warming to room temperature, the material, now a mixture of white crystalline solid and oil, is triturated with 500 ml Et$_2$O for 30 minutes, then is filtered. An insoluble oil passes through the filter funnel with the Et$_2$O and the residue is washed (3 times, 150 ml portions) further with Et$_2$O. After drying on the funnel under a stream of dry N$_2$, 14.14 g (mp 125°–145° C., 39% yield) of the desired product is obtained as white powder. NMR (CDCl$_3$) δ8.85 (bs, 3, —NH$_3$Cl), 4.34 (q, 2, J=7 Hz, OCH$_2$—C), 4.6–4.15 (m, 1, NCHCO$_2$); 3.83 (s, 1, —SH); 1.70 (s, 3, C—CH$_3$), 1.59 (s, 3, C—CH$_3$), 1.35 (t, 3, J=7 Hz, OCH$_2$CH$_3$); IR (KBr): 1725 cm$^{-1}$ (s) (C=O).

Anal. Calcd for C$_7$H$_{16}$ClNO$_2$S: C, 39.34; H, 7.55; N, 6.56. Found: C, 39.04; H, 7.60; N, 6.47.

EXAMPLE 2

Preparation of 21-acetyloxy-9α-fluoro-11α,17α-dihydroxypregn-4-en-20-one-3,2'-spiro(4'-carboethoxy-1',3'-thiazolidine) and the corresponding Δ$^5$ compound Fludrocortisone 21-acetate (2.11 g, 0.005 mole) is dissolved in 80 ml of pyridine and allowed to react with 5.56 g (0.003 mole) of cysteine ethyl ester hydrochloride under a nitrogen atmosphere at room temperature overnight. The pyridine is evaporated at <50° C. in vacuo (9.1 mm) and the residue is triturated with water for 4 hours. The suspension is filtered and the residue is dried to give 2.9 g (mp 148°–154° C.) of the desired product as a yellow amorphous solid which exhibits one spot upon analysis by TLC (silica gel, ether, Rf 0.38). The crude product is suspended in CH$_2$Cl$_2$, the insoluble material is identified as cysteine ethyl ester and the CH$_2$Cl$_2$ suspension is filtered. The filtrate is dried over Na$_2$SO$_4$, concentrated to 35 ml and diluted with 15 ml of heptane to give a total of 0.75 g of a number of fractions of the steroidal thiazolidine (a mixture of Δ$^4$ and Δ$^5$ compounds, with the Δ$^4$ compound predominating), of which 0.33 g (mp 167°–171° C.) is analytically pure. IR (KBr) 3520 and 3400 cm$^{-1}$ (m) (OH and N-H) and 1735 and 1710 cm$^{-1}$ (s) (C=O); NMR (CDCl$_3$) δ5.4–5.2 (m, 1, CH=C), 4.97 (AB quartet, 2, J=18 Hz, Δ$_{ABv}$=13 Hz, CH$_2$—O$_2$CCH$_3$), 4.5–3.8 (m, 2, CH—OH and O$_2$C—CH—N), 4.23 (q, J =7 Hz, 2, CH$_3$CH$_2$—O), 2.07 (s, 3, CH$_3$CO$_2$), 1.41 (s, 3, CH$_3$—C), 1.30 (t, 3, CH$_3$CH$_2$—O), 0.90 (s, 3, CH$_3$—C) and 2.55–1.0 (m, 21, CH$_2$, CH, OH, NH and CH$_2$S); [α]$^{25}$D= +94 (C=0.57, ethanol).

Anal. Calcd for C$_{28}$H$_{40}$SNO$_7$F.H$_2$O: C, 58.82; H, 7.40; N, 2.45. Found: C, 58.65; H, 7.30; N, 2.52.

EXAMPLE 3

Preparation of 21-acetyloxy-9α-fluoro-11β,17α-dihydroxy-16α-methylpregn-4-en-20-one-3,2'-spiro-(4'-carboethoxy-1',3'-thiazolidine) and the corresponding Δ$^5$ compound 21-Acetyloxy-9α-fluoro-11β,17α-dihydroxy-16α-methylpregn-4-ene-3,20-dione (2.18 g, 0.005 mole) is dissolved in 80 ml of pyridine and allowed to react with 5.56 g (0.003 mole) of cysteine ethyl ester hydrochloride under a nitrogen atmosphere at room temperature overnight. The pyridine is evaporated at <50° C. in vacuo (0.1 mm) and the residue is triturated with water for 4 hours. The suspension is filtered and the residue is dried to give the desired product (a mixture of Δ$^4$ and Δ$^5$ compounds).

EXAMPLE 4

Preparation of 21-acetyloxy-9α-fluoro-11β,16α,17α-trihydroxypregn-4-en-20-one-3,2'-spiro (4'-carboethoxy-1',3'-thiazolidine) and the corresponding Δ$^5$ compound 21-Acetyloxy-9α-fluoro-11β,16α,17α-trihydroxy-pregn-4-ene-3,20-dione (2.19 g, 0.005 mole) is dissolved in 80 ml of pyridine and allowed to react with 5.56 g (0.003 mole) of cysteine ethyl ester hydrochloride under a nitrogen atmosphere at room temperature overnight.

The pyridine is evaporated at <50° C. in vacuo (0.1 mm) and the residue is triturated with water for 4 hours. The suspension is filtered and the residue is dried to give the desired product (a mixture of Δ⁴ and Δ⁵ compounds).

EXAMPLE 5

Preparation of 21-acetyloxy-9α-fluoro-11β,17α-dihydroxypregn-4-en-20-one-3,2'-spiro(1',3'-thiazolidine) and the corresponding Δ⁵ compound To 1.2 g (0.0028 mole) of fludrocortisone acetate in 10 ml of pyridine is added 1.7 g (0.015 mole) of 2-aminoethanethiol hydrochloride. The reaction mixture is stirred at room temperature under a nitrogen atmosphere for 24 hours, then the solvent is evaporated. The residue that remains is triturated with CH₂Cl₂ (100 ml) and the suspension that results is filtered. The residue is 2-aminoethanethiol hydrochloride. The filtrate is extracted with 100 ml of water. The CH₂Cl₂ layer is separated, dried over Na₂SO₄ and concentrated in vacuo to give the desired product which is a mixture of Δ⁴ and Δ⁵ compounds.

EXAMPLES 6–30

Substituting the appropriate generally and/or specifically described reactants and/or operating conditions of this invention for those of the preceding examples affords the following compounds of formula (I):

9α-Fluoro-11β,21-dihydroxy-16α,17α-[(1-methylethylidene)-bis (oxy)]pregna-1,4-dien-20-one-3,2'-spiro(4'-carboethoxy-1',3'-thiazolidine);

9α-Fluoro-11β,21-dihydroxy-16α,17α[(1-methylethylidene)-bis(oxy)]pregna-1,4-dien-20-one-3,2'-spiro(4'-carbohexoxy-1',3'-thiazolidine);

9α-Fluoro-11β,21-dihydroxy-16α,17α-[(1-methylethylidene)-bis(oxy)]pregna-1,4-dien-20-one-3,2'-spiro(4'-carbodecoxy-1',3'-thiazolidine);

21-Acetyloxy-9α-fluoro-11β-hydroxy-16α,17α-[(1-methylethylidene)bis(oxy)]pregna-1,4-dien-20-one-3,2'-spiro-(4'-carboethoxy-1',3'-thiazolidine);

21-Acetyloxy-9α-fluoro-11β-hydroxy-16α,17α-[(1-methylethylidene)bis(oxy)]pregna-1,4-dien-20-one-3,2'-spiro(4'-carbohexoxy-1',3'-thiazolidine);

21-Acetyloxy-9α-fluoro-11β-hydroxy-16α,17α-[(1-methylethylidene)bis (oxy)]pregna-1,4-dien-20-one-3,2'-spiro(4'-carbodecosy-1',3'-thiazolidine);

9α-Fluoro-11β,17α,21-trihydroxy-16β-methylpregna-1,4-dien-20-one-3,2'-spiro(4'-carboethoxy-1',3'-thiazolidine);

9α-Fluoro-11β,17α,21-trihydroxy-16β-methylpregna-1,4-dien-20-one-3,2'-spiro(4'-carbohexoxy-1',3'-thiazolidine);

9α-Fluoro-11β,17α,21-trihydroxy-16β-methylpregna-1,4-dien-20-one-3,2'-spiro(4'-carbodecoxy-1',3'-thiazolidine);

9α-Fluoro-11β,17α,21-trihydroxy-16α-methylpregna-1,4-dien-20-one-3,2'-spiro(4'-carboethoxy-1',3'-thiazolidine);

9α-Fluoro-11β,17α,21-trihydroxy-16α-methylpregna-1,4-dien-20-one-3,2'-spiro(4'-carbohexoxy-1',3'-thiazolidine);

9α-Fluoro-11β,17α,21-trihydroxy-16α-methylpregna-1,4-dien-20-one-3,2'-spiro(4'-carbodecoxy-1',3'-thiazolidine);

9α-Fluoro-11β,17α-dihyroxy-16α-methyl-21-valeryloxypregna-1,4-dien-20-one-3,2'-spiro(4'-carboethoxy-1',3'-thiazolidine);

9α-Fluoro-11β,17α-dihydroxy-16β-methyl-21-valeryl-oxypregna-1,4-dien-20-one-3,2'-spiro(4'-carbohexoxy-1',3'-thiazolidine);

9α-Fluoro-11β,17α-dihydroxy-16β-methyl-21-valeryl-oxypregna-1,4-dien-20-one-3,2'-spiro(4'-carbodecoxy-1',3'-thiazolidine);

9α-Fluoro11β,21-dihydroxy-16β-methyl-17α-valeryl-oxypregna-1,4-dien-20-one3,2'-spiro(4'-carboethoxy-1',3'-thiazolidine);

9α-Fluoro-11β,21-dihydroxy-16β-methyl-17α-valeryl-oxypregna-1,4 -dien-20-one-3,2'-spiro(4'-carbohexoxy-1',3'-thiazolidine);

9α-Fluoro-11β,21-dihydroxy-16β-methyl-17α-valeryl-oxypregna-1,4-dien-20-one-3,2'-spiro(4'-carbodecoxy-1',3'-thiazolidine);

9α-Fluoro-11β,17α,21-trihydroxy-16β-methylpregna-1,4-dien-20-one-3,2'- spiro(4'-carboethoxy-5',5'-dimethyl-1',3'-thiazolidine);

9α-Fluoro-11β,17α,21-trihydroxy-16α-methylpregna-1,4-dien-20-one-3,2'-spiro(4'-carbohexoxy-5',5'-dimethyl-1',3'-thiazolidine);

9α-Fluoro-11β,17α,21-trihydroxy-16α-methylpregna-1,4-dien-20-one-3,2'-spiro(4'-carbodecoxy-5',5'-dimethyl-1',3'-thiazolidine);

21-chloro-9α-fluoro-11β,17α-dihydroxypregn-4-en-20-one-3,2'-spiro(4'-carboethoxy-1',3'-thiazolidine) and the corresponding Δ⁵ compound;

21-chloro-9α-fluoro-11β,17α-dihydroxypregn-4-en-20-one-3,2'-spiro(4'-carbomethoxy-1',3'-thiazolidine) and the corresponding Δ⁵ compound;

21-chloro-6α-fluoro-11β,17α-dihydroxypregn-4-en-20-one-3,2'-spiro(4'-carbodecoxy-1',3'-thiazolidine) and the corresponding Δ⁵ compound; and 9α-fluoro-11β,21-dihydroxy-16α,17α-[(1-methylethylidene)bis(oxy)] pregna-1,4-dien-20-one-3,2'-spiro(1',3'-thiazolidine).

EXAMPLES 31–51

Following the procedures described hereinabove, using the appropriate specific reactants, affords the following additional compounds according to the invention:

| Example Number | Z | R₁ | R₂ | R₃ | R₄ | R₅ | R₆ | R₉ | R₁₀ | R₁₁ | Δ |
|---|---|---|---|---|---|---|---|---|---|---|---|
| 31 | =O | H | α-OH | H | H | —COOC₄H₉ | —OCOCH₃ | H | H | α-Cl | 1,2 and 4,5 |
| 32 | β-OH | H | α-OH | H | H | —COOCH₃ | —OH | H | H | α-F | 1,2 and 4,5 |
| 33 | β-OH | H | together with R₉ = | —CH₃ | —CH₃ | —COOC₂H₅ | —OH | See R₂ | H | α-F | 1,2 and 4,5 mixture |

EXAMPLES 31-51-continued

Following the procedures described hereinabove, using the appropriate specific reactants, affords the following additional compounds according to the invention:

| Example Number | Z | R₁ | R₂ | R₃ | R₄ | R₅ | R₆ | R₉ | R₁₀ | R₁₁ | Δ |
|---|---|---|---|---|---|---|---|---|---|---|---|
| | | | $-O\diagdown_{C}\diagup^{CH_3}_{CH_3}$ $-O\diagup~^{~}\diagdown^{~}$ | | | | | | | | of 4,5 and 5,6 |
| 34 | β-OH | α-F | together with R₉ = $-O\diagdown_{C}\diagup^{CH_3}_{CH_3}$ $-O\diagup~^{~}\diagdown^{~}$ | —CH₃ | —CH₃ | —COOH | —OH | See R₂ | $-\overset{O}{\overset{\|}{C}}-H$ | α-F | 1,2 and 4,5 |
| 35 | β-OH | H | α-OH | H | H | $-\overset{O}{\overset{\|}{C}}OC_6H_5$ | —OCOCH₃ | β-CH₃ | $-\overset{O}{\overset{\|}{C}}OC_6H_5$ | α-F | 1,2 and 4,5 |
| 36 | β-OH | H | together with R₉ = $-O\diagdown_{C}\diagup^{CH_3}_{CH_3}$ $-O\diagup~^{~}\diagdown^{~}$ | H | H | $-\overset{O}{\overset{\|}{C}}OCH_2C_6H_5$ | —OCOCH₃ | See R₂ | $-\overset{O}{\overset{\|}{C}}OCH_2C_6H_5$ | α-F | 1,2 and 4,5 |
| 37 | β-OH | α-F | —OCOC₂H₅ | H | H | —COOC₆H₁₃ | —OCOC₂H₅ | β-CH₃ | H | H | 1,2 and 4,5 |
| 38 | β-OH | α-F | α-OH | H | H | —COOC₁₀H₂₁ | —OH | α-OH | H | H | 1,2 and 4,5 |
| 39 | β-OH | α-F | α-OH | H | H | —COOC₆H₁₃ | —Cl | H | H | H | mixture of 4,5 & 5,6 |
| 40 | β-OH | α-F | α-OH | —CH₃ | —CH₃ | —COOH | —Cl | β-CH₃ | $-\overset{O}{\overset{\|}{C}}\diagdown_H$ | H | 1,2 and 4,5 |
| 41 | =O | α-F | α-OH | —CH₃ | —Ch₃ | —COOC₂H₅ | —Cl | β-CH₃ | H | H | 1,2 and 4,5 |
| 42 | β-OH | α-F | together with R₉ = $-O\diagdown_{C}\diagup^{C_2H_5}_{C_2H_5}$ $-O\diagup~^{~}\diagdown^{~}$ | H | H | —COOC₆H₁₃ | —OH | See R₂ | H | H | 1,2 and 4,5 |
| 43 | β-OH | α-F | together with R₉ = $-O\diagdown_{C}\diagup^{CH_3}_{C_6H_5}$ $-O\diagup~^{~}\diagdown^{~}$ | H | H | —COOC₆H₁₃ | —OH | See R₂ | H | H | 1,2 and 4,5 |
| 44 | β-OH | α-F | —OCOC₃H₇ | H | H | —COOC₂H₅ | —OCOCH₃ | H | H | α-F | 1,2 and 4,5 |
| 45 | β-OH | α-F | α-OH | H | H | —COOC₁₀H₂₁ | —OH | α-CH₃ | H | α-F | 1,2 and 4,5 |
| 46 | β-OH | α-F | α-OH | H | H | H | —OCOC(CH₃)₃ | α-CH₃ | H | α-F | 1,2 and 4,5 |
| 47 | β-OH | H | together with R₉ = | H | H | H | —OCOCH₃ | See R₂ | H | α-F | 1,2 and |

EXAMPLES 31-51-continued

Following the procedures described hereinabove, using the appropriate specific reactants, affords the following additional compounds according to the invention:

| Example Number | Z | $R_1$ | $R_2$ | $R_3$ | $R_4$ | $R_5$ | $R_6$ | $R_9$ | $R_{10}$ | $R_{11}$ | Δ |
|---|---|---|---|---|---|---|---|---|---|---|---|
| 48 | β-OH | α-F | together with $R_9$ = $-O\diagdown C \diagup CH_3$ / $-O\diagup \diagdown CH_3$ | H | H | $-COOC_6H_{13}$ | $-OH$ | See $R_2$ | H | α-F | 1,2 and 4,5 |
| 49 | β-OH | α-F | together with $R_9$ = $-O\diagdown C \diagup CH_3$ / $-O\diagup \diagdown CH_3$ | H | H | $-COOC_{10}H_{21}$ | $-OCOCH_3$ | See $R_2$ | H | α-F | 1,2 and 4,5 |
| 50 | β-OH | H | α-OH | H | H | $-COOC_2H_5$ | $-OCOCH_3$ | α-$CH_3$ | H | α-F | 1,2 and 4,5 |
| 51 | β-OH | α-F | α-OH | H | H | H | $-OH$ | α-OH | H | H | 1,2 and 4,5 |

The compounds of the present invention are conveniently administered to warm-blooded animals via conventional oral or topical administration with any suitable nontoxic pharmaceutically acceptable oral or topical inert carrier material. Such carrier materials are well-known to those skilled in the art of oral and topical pharmaceutical formulations. For those not skilled in the art, reference is made to the text entitled, "REMINGTON'S PHARMACEUTICAL SCIENCES," (fourteenth Edition), 1970. In a typical preparation for oral adminstration, e.g., tablet or capsule, any one of the compounds of the instant invention is combined in an antiinflammatory effective amount with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD&C dyes.

Similarly, in a typical formulation for topical application, any one of the compounds of the instant invention is combined with triacetin, such that the active ingredient is present in an antiinflammatory effective amount. The preparation is simply applied topically to the inflamed area, whereby the therapeutically active compound is dermally absorbed and "cleaved" to release the parent steroidal moiety at the site of inflammation.

Naturally, the therapeutic dosage range for the compounds of the instant invention will vary with the size and needs of the patient. However, generally speaking, the following dosage guidelines will suffice. On an oral basis, the therapeutic dose required for a compound of the instant invention will generally, on a molecular basis, mimic that for the parent conventional steroid moiety (e.g., fludrocortisone acetate, triamcinolone acetonide, betamethasone, dexamethasone, or the like). On a topical basis, application of an 0.01% to 2.5% concentration of a compound of the instant invention (in a suitable topical carrier material) to the site of inflammation should suffice.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What we claim is:

1. A compound having the structural formula

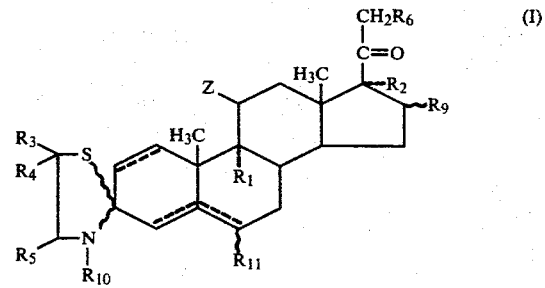

wherein $R_1$ and $R_{11}$ are each H, F or Cl, with the proviso that $R_1$ and $R_{11}$ cannot simultaneously be H; $R_2$ is OH, —OCOC$_7$, —OCOC$_8$ or C$_1$–C$_{10}$ alkyl; R$_3$ and R$_4$ may be the same or different and are each H or C$_1$–C$_8$ alkyl; R$_5$ is H or —COOR$_7$; R$_6$ is OH, F, Cl, Br or —OCOR$_8$; R$_7$ is H, C$_1$–C$_{20}$ alkyl, C$_2$–C$_{20}$ alkenyl, C$_5$–C$_7$ cycloalkyl, C$_5$–C$_7$ cycloalkyl-C$_6$–C$_{10}$ aryl, phenyl or C$_1$–C$_4$ alkylsubstituted phenyl; R$_8$ is C$_1$–C$_{20}$ alkyl, C$_2$–C$_{20}$ alkenyl, C$_5$–C$_7$ cycloalkyl, C$_5$–C$_7$ cycloalkyl-C$_6$–C$_{10}$ aryl, phenyl, C$_1$–C$_4$ alkyl-substituted phenyl, —(CH$_2$)$_n$COOH wherein n is an integer of 1 to 5, or —(CH$_2$)$_n$CON(R$_7$)$_2$ wherein n and R$_7$ are defined as above, or R$_8$ is

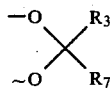

or a 2, 3 or 4 pyridyl, wherein at least one of the hydrogen atoms therein can be replaced by a member selected from the group consisting of —N(R$_4$)$_2$, —CON(R$_4$)$_2$, —SOR$_4$, a halogen atom (Cl, Br, I), —COOR$_4$, —COOCH$_2$N(R$_4$)$_2$ and —COOCH$_2$—S—R$_4$, wherein R$_4$ is defined above; R$_9$ is H, C$_1$–C$_8$ alkyl, F, Cl or OH; or R$_2$ and R$_9$ may be combined to form a cyclic ketal of the formula

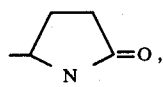

wherein R$_3$ and R$_7$ are defined as above; R$_{10}$ is H, —COR$_7$ or —COOR$_7$ wherein R$_7$ is defined as above, with the proviso that when R$_{10}$ is H, then the compound of formula (I) can be in the form of a pharmaceutically acceptable acid addition salt; Z is =O, β—OH or β—O-COR$_7$ wherein R$_7$ is defined as above; the dotted line at the 1(2)-position indicates the presence of an optional double bond; the dotted lines at the 4(5) and 5(6) positions indicate the presence of a double bond at either the 4(5) or the 5(6) position; and the wavy lines indicate the α or β configuration.

2. A compound of claim 1 wherein double bonds are present in both the 1(2) and the 4(5) positions.

3. A compound of claim 1 wherein the steroid nucleus contains one double bond.

4. A compound of claim 3 wherein the double bond is present in the 4(5) position.

5. A compound of claim 3 wherein the double bond is present in the 5(6) position.

6. A compound of claim 1 wherein Z is =O.

7. A compound of claim 1 wherein Z is β—OH.

8. A compound of claim 1 wherein R$_1$ is α—F and R$_{11}$ is H.

9. A compound of claim 1 wherein R$_1$ is α—Cl and R$_{11}$ is H.

10. A compound of claim 1 wherein R$_1$ is H and R$_{11}$ is α—F.

11. A compound of claim 1 wherein R$_1$ and R$_2$ are each α—F.

12. A compound of claim 1 or 8 wherein R$_2$ is OH.

13. A compound of claim 1 or 8 wherein R$_2$ and R$_9$ are combined to form a cyclic ketal of the formula

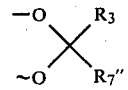

wherein R$_3$ is H or C$_1$–C$_8$ alkyl and R$_7''$ is H, C$_1$–C$_8$ alkyl or phenyl.

14. A compound of claim 13 wherein R$_3$ is methyl or ethyl and R$_7''$ is methyl, ethyl or phenyl.

15. A compound of claim 1 or 8 wherein R$_2$ is —OCO(alkyl) wherein the alkyl portion contains 1 to 8 carbon atoms.

16. A compound of claim 1 wherein R$_3$ and R$_4$ are each H.

17. A compound of claim 1 wherein R$_3$ and R$_4$ are each methyl.

18. A compound of claim 1 wherein R$_5$ is H.

19. A compound of claim 1 wherein R$_5$ is —COOR$_7'$ wherein R$_7'$ is H, C$_1$–C$_{20}$ alkyl or benzyl.

20. A compound of claim 19 wherein R$_7'$ is C$_1$–C$_4$ alkyl.

21. A compound of claim 19 wherein R$_7'$ is C$_5$–C$_{20}$ alkyl.

22. A compound of claim 1 or 8 wherein R$_6$ is OH.

23. A compound of claim 1 or 8 wherein R$_6$ is Cl.

24. A compound of claim 1 or 8 wherein R$_6$ is —OCO(alkyl) wherein the alkyl portion contains 1 to 8 carbon atoms.

25. A compound of claim 1 or 8 wherein R$_9$ is H.

26. A compound of claim 1 or 8 wherein R$_9$ is α—CH$_3$.

27. A compound of claim 1 or 8 wherein R$_9$ is β—CH$_3$.

28. A compound of claim 1 or 8 wherein R$_9$ is α—OH.

29. A compound of claim 1 wherein R$_{10}$ is H.

30. A compound of claim 1 wherein R$_3$, R$_4$, R$_5$ and R$_{10}$ are as defined in claim 1 and the remainder of the structural variables are identical to those of a known anti-inflammatory halogen-containing steroid selected from the group consisting of fludrocortisone, fludrocortisone acetate, flurandrenolone acetonide, amcinafide, betamethasone, betamethasone benzoate, amcinafal, betamethasone valerate, betamethasone dipropionate, chloroprednisone acetate, dexamethasone, difluprednate, flumethasone, flumethasone pivalate, flunisolide acetate, fluocinolone acetonide, fluocinonide, fluprednisolone, fluprednisolone valerate, paramethasone, paramethasone acetate, triamcinolone, triamcinolone acetonide, triamcinolone hexacetonide and triamcinolone diacetate.

31. A compound of claim 30 wherein R$_3$ and R$_4$ are each hydrogen or methyl, R$_5$ is —COOR$_7'$ wherein R$_7'$ is H, C$_1$–C$_{20}$ alkyl or benzyl, and R$_{10}$ is H.

32. A compound of claim 31 wherein R$_7'$ is alkyl of 1 to 12 carbon atoms.

33. The compound of claim 1 which is 21-acetyloxy-9α-fluoro-11β,17α-dihydroxypregn-4-en-20-one-3,2'-spiro(4'-carboethoxy-1',3'-thiazolidine).

34. The compound of claim 1 which is 21-acetyloxy-9α-fluoro-11β,17α-dihydroxypregn-5-en-20-one-3,2'-spiro(4'-carboethoxy-1',3'-thiazolidine).

35. The compound of claim 1 which is 21-acetyloxy-9α-fluoro-11β,17α-dihydroxy-16α-methylpregn-4-en-20-one-3,2'-spiro(4'-carboethoxy-1',3'-thiazolidine).

36. The compound of claim 1 which is 21-acetyloxy-9α-fluoro-11β,17α-dihydroxy-16α-methylpregn-5-en-20-one-3,2'-spiro(4'-carboethoxy-1',3'-thiazolidine).

37. The compound of claim 1 which is 21-acetyloxy-9α-fluoro-11β,16α,17α-trihydroxypregn-4-en-20-one-3,2'-spiro(4'-carboethoxy-1',3'-thiazolidine).

38. The compound of claim 1 which is 21-acetyloxy-9α-fluoro-11β,16α,17α-trihydroxypregn-5-en-20-one-3,2'-spiro(4'-carboethoxy-1',3'-thiazolidine).

39. The compound of claim 1 which is 9α-fluoro-11β,21-dihydroxy-16α,17α-[(1-methylethylidene)-bis(oxy)]pregna-1,4-dien-20-one-3,2'-spiro(4'-carboethoxy-1',3'-thiazolidine).

40. The compound of claim 1 which is 9α-fluoro-11β,21-dihydroxy-16α,17α-[(1-methylethylidene)bis(oxy)]pregna-1,4-dien-20-one-3,2'-spiro(4'-carbohexoxy-1',3'-thiazolidine).

41. The compound of claim 1 which is 9α-fluoro-11β,21-dihydroxy-16α,17α-[(1-methylethylidene)bis(oxy)]-pregna-1,4-dien-20-one-3,2'-spiro(4'-carbodecoxy-1',3'-thiazolidine).

42. The compound of claim 1 which is 21-acetyloxy-9α-fluoro-11β-hydroxy-16α,17α-[(1-methylethylidene)-bis(oxy)pregna-1,4-dien-20-one-3,2'-spiro(4'-carboethoxy-1',3'-thiazolidine).

43. The compound of claim 1 which is 21-acetyloxy-9α-fluoro-11β-hydroxy-16α,17α-[(1-methylethylidene)-bis(oxy)]pregna-1,4-dien-20-one-3,2'-spiro(4'-carbohexoxy-1',3'-thiazolidine).

44. The compound of claim 1 which is 21-acetyloxy-9α-fluoro-11β-hydroxy-16α,17α-[(1-methylethylidene)-bis(oxy)]pregna-1,4-dien-20-one-3,2'-spiro(4'-carbodecoxy-1',3'-thiazolidine).

45. The compound of claim 1 which is 9α-fluoro-11β,17α,21-trihydroxy-16β-methylpregna-1,4-dien-20-one-3,2'-spiro(4'-carboethoxy-1',3'-thiazolidine).

46. The compound of claim 1 which is 9α-fluoro-11β,17α,21-trihydroxy-16β-methylpregna-1,4-dien-20-one-3,2'-spiro(4'-carbohexoxy-1',3'-thiazolidine).

47. The compound of claim 1 which is 9α-fluoro-11β,17α,21-trihydroxy-16β-methylpregna-1,4-dien-20-one-3,2'-spiro(4'-carbodecoxy-1',3'-thiazolidine).

48. The compound of claim 1 which is 9α-fluoro-11β,17α,21-trihydroxy-16α-methylpregna-1,4-dien-20-one-3,2'-spiro(4'-carboethoxy-1',3'-thiazolidine).

49. The compound of claim 1 which is 9α-fluoro-11β,17α,21-trihydroxy-16α-methylpregna-1,4-dien-20-one-3,2'-spiro(4'-carbohexoxy-1',3'-thiazolidine).

50. The compound of claim 1 which is 9α-fluoro-11β,17α,21-trihydroxy-16α-methylpregna-1,4-dien-20-one-3,2'-spiro(4'-carbodecoxy-1',3'-thiazolidine).

51. The compound of claim 1 which is 9α-fluoro-11β,17α,21-trihydroxy-16α-methylpregna-1,4-dien-20-one-3,2'-spiro(4'-carboethoxy-5',5'-dimethyl-1',3'-thiazolidine).

52. The compound of claim 1 which is 9α-fluoro-11β,17α,21-trihydroxy-16α-methylpregna-1,4-dien-20-one-3,2'-spiro(4'-carbohexoxy-5',5'-dimethyl-1',3'-thiazolidine).

53. The compound of claim 1 which is 9α-fluoro-11β,17α,21-trihydroxy-16α-methylpregna-1,4-dien-20-one-3,2'-spiro(4'-carbodecoxy-5',5'-dimethyl-1',3'-thiazolidine).

54. The compound of claim 1 which is 9α-fluoro-11β,17α-dihydroxy-16β-methyl-21-valeryloxypregna-1,4-dien-20-one-3,2'-spiro(4'-carboethoxy-1',3'-thiazolidine).

55. The compound of claim 1 which is 9α-fluoro-11β,17α-dihydroxy-16β-methyl-21-valeryloxypregna-1,4-dien-20-one-3,2'-spiro(4'-carbohexoxy-1',3'-thiazolidine).

56. The compound of claim 1 which is 9α-fluoro-11β,17α-dihydroxy-16β-methyl-21-valeryloxypregna-1,4-dien-20-one-3,2'-spiro(4'-carbodecoxy-1',3'-thiazolidine).

57. The compound of claim 1 which is 9α-fluoro-11β,21-dihydroxy-16β-methyl-17α-valeryloxypregna-1,4-dien-20-one-3,2'-spiro(4'-carboethoxy-1',3'-thiazolidine).

58. The compound of claim 1 which is 9α-fluoro-11β,21-dihydroxy-16β-methyl-17α-valeryloxypregna-1,4-dien-20-one-3,2'-spiro(4'-carbohexoxy-1',3'-thiazolidine).

59. The compound of claim 1 which is 9α-fluoro-11β,21-dihydroxy-16β-methyl-17α-valeryloxypregna-1,4-dien-20-one-3,2'-spiro(4'-carbodecoxy-1',3'-thiazolidine).

60. The compound of claim 1 which is 21-chloro-9α-fluoro-11β,17α-dihydroxypregn-4-en-20-one-3,2'-spiro(4'-carboethoxy-1',3'-thiazolidine).

61. The compound of claim 1 which is 21-chloro-9α-fluoro-11β,17α-dihydroxypregn-5-en-20-one-3,2'-spiro(4'-carboethoxy-1',3'-thiazolidine).

62. The compound of claim 1 which is 21-chloro-9α-fluoro-11β,17α-dihydroxypregn-4-en-20-one-3,2'-spiro(4'-carbomethoxy-1',3'-thiazolidine).

63. The compound of claim 1 which is 21-chloro-9α-fluoro-11β,17α-dihydroxypregn-5-en-20-one-3,2'-spiro(4'-carbomethoxy-1',3'-thiazolidine).

64. The compound of claim 1 which is 21-chloro-9α-fluoro-11β,17α-dihydroxypregn-4-en-20-one-3,2'-spiro(4'-carbodecoxy-1',3'-thiazolidine).

65. The compound of claim 1 which is 21-chloro-9α-fluoro-11β,17α-dihydroxypregn-5-en-20-one-3,2'-spiro(4'-carbodecoxy-1',3'-thiazolidine).

66. A pharmaceutical composition of matter useful in alleviating inflammation in or on a warm-blooded animal which comprises an anti-inflammatory effective amount of a compound as defined by claim 1, in combination with a nontoxic pharmaceutically acceptable oral or topical inert carrier therefor.

67. A method for alleviating inflammation in or on a warm-blooded animal exhibiting an inflammatory response which comprises orally or topically administering thereto an antiinflammatory effective amount of a compound as defined by claim 1, in combination with a nontoxic pharmaceutically acceptable oral or topical inert carrier therefor.

* * * * *